United States Patent [19]

Dye

[11] Patent Number: 4,971,044

[45] Date of Patent: Nov. 20, 1990

[54] METHOD OF MANUFACTURING A COMPRESSIBLE SLEEVE

[75] Inventor: John F. Dye, Bridgewater, Mass.

[73] Assignee: The Kendall Company, Boston, Mass.

[21] Appl. No.: 324,114

[22] Filed: Mar. 16, 1989

[51] Int. Cl.[5] ................................................ A61F 5/00

[52] U.S. Cl. ............................... 128/87 R; 128/24 R; 128/89 R

[58] Field of Search ................. 128/24 R, 87 R, 89 R, 128/89 A, 90, DIG. 20, 84 C, 85

[56] References Cited

U.S. PATENT DOCUMENTS 3,164,152 1/1965 Vere Nicoll ...................... 128/87 R
3,548,809 12/1970 Conti ................................ 128/24 R
3,824,992 7/1974 Nicholson et al. ............... 128/24 R
4,402,312 9/1983 Villari et al. ...................... 128/24 R

*Primary Examiner*—Robert A. Hafer
*Assistant Examiner*—Lynda M. Cofsky
*Attorney, Agent, or Firm*—Alvin Isaacs

[57] ABSTRACT

A method for the manufacture of a limb compressible sleeve to permit the sequential distal to proximal compression of the limb, comprising fabricating a pair of elongated sheets, aligning them together, sealing chamber lines between the sheets, folding one end of the pair of sheets onto itself and sealing the longitudinal sides together to define as sheath into which a patient may insert a limb.

5 Claims, 2 Drawing Sheets

METHOD OF MANUFACTURING A COMPRESSIBLE SLEEVE

BACKGROUND OF THE INVENTION

1. Field of the Invention

This invention relates to pressurizable, multichambered, therapeutic devices, and more particularly to methods of manufacturing sleeves for applying compressive pressures against a patient's leg.

2. Prior Art

Blood flow in patient's extremities, particularly the legs, markedly decrease during extended terms of confinement. Such pooling or stasis, is particularly acute in surgery and during recovery periods immediately thereafter.

Blood flow compressive devices, such as shown in U.S. Pat. Nos. 4,013,069 and 4,030,488, incorporated herein by reference, develop and facilitate the application of compressive pressures against a patient's limbs and in so doing promoting venous return. The devices comprise a pair of sleeves which are wrapped about the patient's limbs, with a controller for supplying the pressurized fluid to the sleeves.

These sleeve devices may be seen in U.S. Pat. Nos. 4,402,312 and 4,320,746, which are also incorporated herein by reference.

One use for the above mentioned sleeves is the prevention of deep vein thrombosis (DVT) which sometimes occurs in surgical patients who are confined to bed. When a DVT occurs, the valves that are located within the veins of the leg can be damaged which in turn can cause stasis and high pressure in the veins of the lower leg. Patients who have this condition often have leg swelling (edema) and tissue breakdown (venous stasis ulcer) in the lower leg.

It has been shown that pneumatic compression can be highly effective in the treatment of such edema and venous ulcers. This treatment is usually performed by the patient themselves at home on a daily basis and requires that the patient be able to put on and remove the sleeves unassisted. The sleeve devices which are wrappable from a flat configuration as shown in the aforementioned patents, are difficult to apply by the patients themselves.

It is therefore an object of the present invention, to provide a compressible sleeve device which is easily utilizable at home by the patient himself.

A further object of the present invention is to prepare a compressible sleeve device for optimizing therapy for venous ulcers and edema associated with poor venous return.

BRIEF SUMMARY OF THE INVENTION

The present invention comprises a method of making an elongated compressible sleeve device for enclosing a length of a patients limb, the sleeve having a plurality of sets of adjoining laterally extending fluid pressure chambers. Devices of this description are described and claimed in copending application Ser. No. 324.513 of John F. Dye, filed concurrently.

The sleeve is comprised of a single elongated outermost sheet of flexible fluid-impervious material such as urethane-coated nylon.

An "inner" film of a suitable flexible material such as urethane is disposed against the upper side of the "outer" elongated sheet, having common sealed peripheral margins. The film is sealed with respect to the outer sheet to define a plurality of pressurizable chambers. The outer sheet is most preferably stiffer and inelastic relative to the inner film, thereby permitting the inner layer to conform appreciably better to the shape of the leg. Thus, the outer sheet will remain relatively flat upon inflation while the inner film inflates and the areas of the film defining adjacent chambers press together, which in turn substantially inhibits zero pressure areas. The elongated sheet and attached film is folded upon itself along a transverse fold near its longitudinal midpoint. The sheet is then joined along all of one and a portion of its other longitudinal edges when folded upon itself to leave one side open from the midpoint upwardly for ease of inserting the limb, thereby forming a two-layered sheath-like structure, open at its proximal end to define an inner film and outer sheet arrangement. A plurality of conduits are arranged in fluid communication with their respective chambers, each conduit terminating in a connector adjacent the open end of the sleeve.

The sleeve has a distal end which is closed by its transverse fold, for the enclosed emplacement of a patient's foot. An oblong or generally oval non-inflatable pad is preferably enclosed between the inner and outer sheets at the distal end of the sleeve, on top of the film, to provide a cushion base for the patient's foot.

The outer film of the topmost layer is positionable over the front side of a patient's limb. An adhering or securement means is disposed along the front of the topmost layer.

The side edges of the topmost layer, from the proximal end of the foot chamber, to the uppermost end of the sleeve, have an adhering strip attached therealong. The longitudinal side portions of the sleeve include margins or flap portions which are foldable onto the adhering means, so as to adjustably encase the wearer's limb in the sleeve.

The topmost layer comprises a pair of longitudinally directed pressurizable chambers which are in fluid communication with the pressurizable chamber above and alongside the patient's foot.

A longitudinally directed centrally disposed sight line may be arranged along the middle of the adhering means to permit the patient to line up the sleeve, so that the sight line is aligned up the middle of the limb, permitting most effective utilization of the compressive chambers on the limb.

When the sleeve fully encloses a patient's limb, and the marginal side flaps of the sleeve are wrapped over and stuck to their respective sides of the adhering means, the patient's limb is almost completely surrounded by inflatable chambers, awaiting sequential pressurization. However, the front of a patient's leg is bony and hence requires no pressurizable chambers. The important area is the muscular area on the sides and back of a patient's leg, which contains the veins to which compressive pressure need be applied in accordance with this invention. The front side of the sleeve, which comprises the tongue portion thereof, is inelastic, so that when compression occurs in the remainder of the sleeve and onto the leg, tension is applied across the curvature of the tongue which in effect translates into pressure over the radius of curvature along the front of a patient's leg.

BRIEF DESCRIPTION OF THE DRAWINGS

The objects and advantages will become more apparent when viewed in conjunction with the following drawings, in which.

DESCRIPTION OF THE PREFERRED EMBODIMENT

The present invention comprises a method of making an elongated compressible sleeve 10 for enclosing a patient's limb, such as a leg. The sleeve 10, shown in perspective view in FIG. 1, includes a plurality of adjoining generally transversely extending fluid pressurizable chambers 12, which are shown more clearly in FIG. 4.

Figure 3:
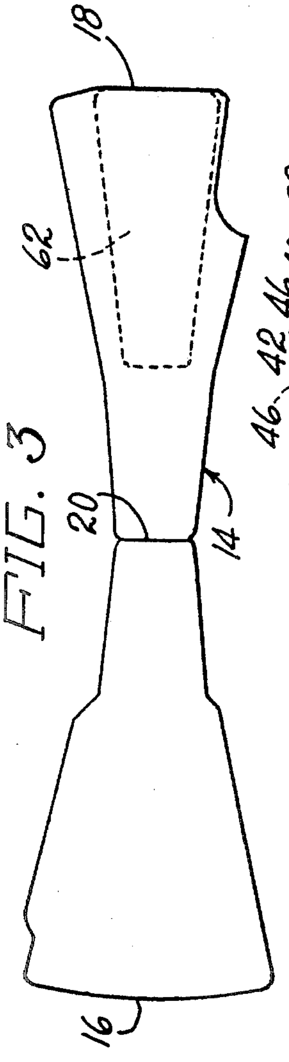
FIG. 3 is a plan view of the elongated outer sheet, which when folded generally along its transverse midpoint, comprises the outer layer of the sleeve.

The sleeve 10 is comprised of an outermost flexible fluid-impervious sheet 14, made of urethane-coated nylon, or the like, in an elongated form, as shown in FIG. 3. The outermost sheet 14 has a first end 16 and a second or opposed end 18, each of which has a transverse dimension that narrows (tapers) slightly to a general mid-point of the sheet 14, defined by a transverse fold line 20.

Figure 4:
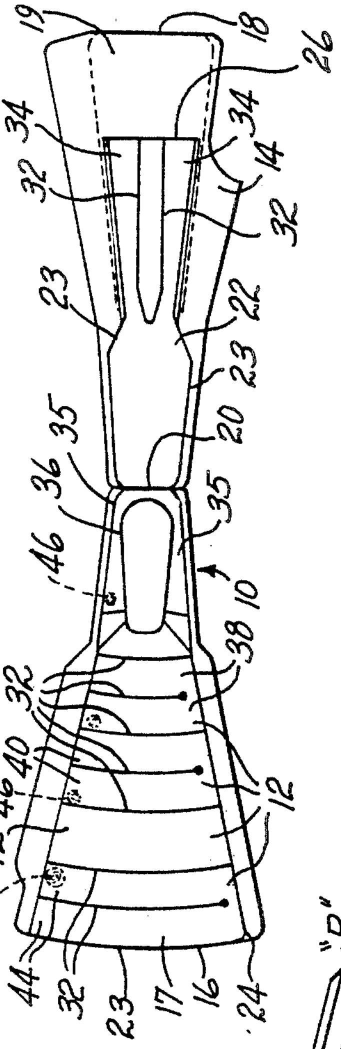
FIG. 4 is a plan view of an inner film disposed upon the outer sheet having the chambers defined by seal margins between the inner film and the outer sheet.

The sleeve 10 is also comprised of an innermost flexible fluid-impervious film 22, made of plastic material such as urethane, having a peripheral outline, as shown in FIG. 4, which is generally similar to the configuration of the outermost sheet 14. As previously stated, the outermost sheet is stiffer and inelastic relative to the innermost film so that the latter conforms well to the shape of the leg while the former remains relatively flat upon inflation.

The film 22 has a first end 24 and a second end 26, each of which has a transverse dimension that narrows slightly to a general mid-point of the film 22 defined by the common transverse "fold" line 20. The peripheral outline of the innermost film 22 is substantially the same as the periphery of the outermost sheet 14. Preferably, however, the length of the film 22, to the right of the common "fold" line 20 as shown in FIG. 4, is shorter than the corresponding length of the outer sheet 14, e.g. on the order of 20% shorter.

Figure 2:
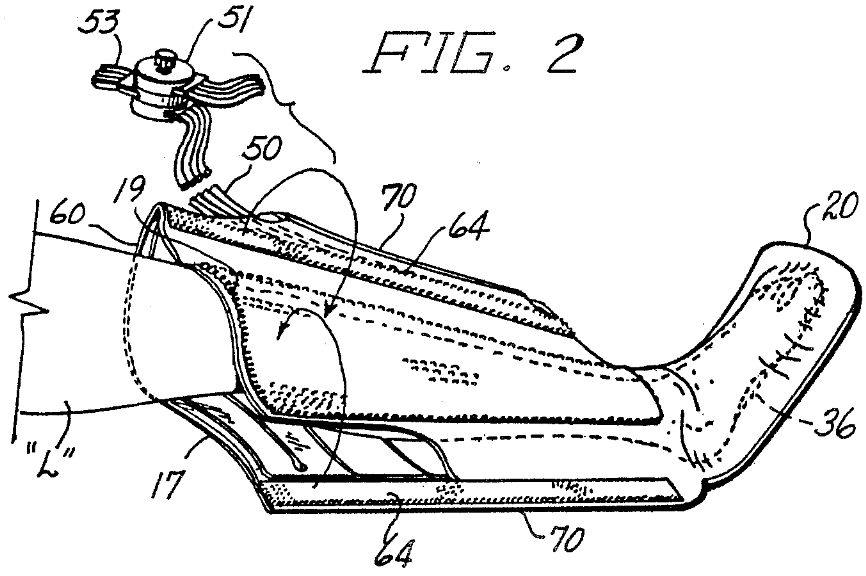
FIG. 2 is another perspective view of the sleeve shown in FIG. 1, with a patient's limb depicted therein.

In both the outermost sheet 14, and the innermost film 22, the longer portion of each to one side of their common fold line 20, comprises the backside portion 17 of the sleeve 10 having elongated side marginal portions 70 which wrap about the patient's limb from the backside thereat, which portions are to the left of the fold line 20, viewing FIG. 2.

The innermost film 22 is placed over the outermost sheet 14, with their common fold line 20 and their first ends 24 and 16 contiguous, as shown in FIG. 4. The section of the sleeve 10, to the right of the fold line 20, as shown in FIG. 4, comprises the frontside portion 19, of the sleeve 10, when the film 22 and sheet 14 are folded along the fold line 20, onto themselves, to form the sleeve.

The innermost film 22 may then be sealed to the outermost sheet 14 generally at the periphery 23 of film 22 and at seal lines 32 which also define a plurality of longitudinally directed constant pressure chambers 12 between the innermost film 22 and the outermost sheet 14, the seal lines 32 and chambers 12 being shown in FIG. 4 prior to the folding of the elongated sheet 14 and film 22 and subsequent peripheral joining. Suitable sealing means, e.g. radio frequency (RF) sealing means, will be readily suggested to those skilled in the art.

A foot pad 36, of generally oval shape, is non-pressurizably disposed between the sheet 14 and the film 22, to form a cushion against which a patient's foot is placed, as may be seen in FIG. 2. A front pressurizable chamber 34, partially bifurcated, is disposed to the right of the fold line 20 of FIG. 4, the front chamber 34 being in fluid communication with a chamber 35 which extends around the side portions of the foot pad 36. The bifurcated chamber 34 eliminates any pressure chamber juxtaposed against the very forwardmost bony part of a patient's leg, when it is enclosed in the sleeve 10. This in turn applies compression to the flat leg sections on either side of the forwardmost bony portion of the lower leg. Since these flat leg sections are the sites of many ulcers, it follows that they are important areas for applying compressive pressure in accordance with this invention. The backside portion 17 of the sleeve 10 includes a lowermost pressurizable ankle chamber 38, an intermediate calf chamber 40, a first thigh chamber 42 and an upper thigh chamber 44. Each chamber 38, 40, 42 and 44 has an orifice 46 for the sequential pressurization and de-pressurization of those chambers, through a plurality of conduits 50, through a coupling adapter 51, which is in fluid communication through further conduits 53 with a compression generator, as identified in various patents including those previously incorporated by reference herein. The chamber 35, disposed about the sides and forepart of the pad 36, as well as the pressurizable chamber 34 in the frontside of the sleeve 10, including the top of the foot, is maintained at a constant base pressure of about 10 pounds pressure, from a pressure generating source as aforementioned.

Figure 5:
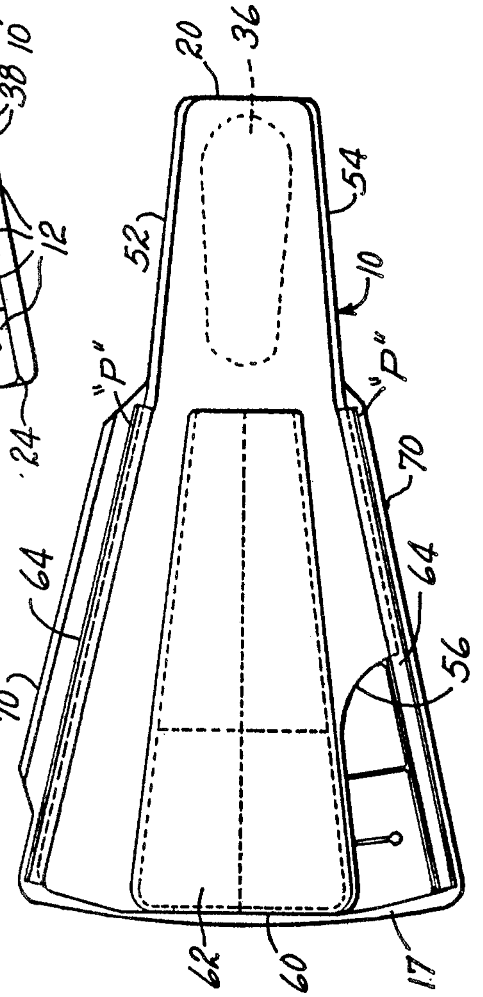
FIG. 5 is a plan view of the sleeve, with the inner and the outer sheet joined at their appropriate peripheral locations.

During assembly of the sleeve 10, the frontside 19 of the sleeve 10 is folded over onto the backside portion 17 of the sleeve 10, along their common fold line 20, and are joined, as by stitching or the like, along only their common peripheral points, as indicated by "P", shown in FIG. 5. The common peripheral points P may be recited as one generally longitudinally common side edge 52, and another side edge 54, only a portion of which is common to the frontside 19 and the backside 17. A longitudinal opening 56 extends almost half-way along one longitudinal side, and the sleeve 10 is open at its proximalmost end 60, to permit, in conjunction with the side opening 56, a patient to easily slide his leg "L" into the sheath-like arrangement of the sleeve 10.

Figure 1:
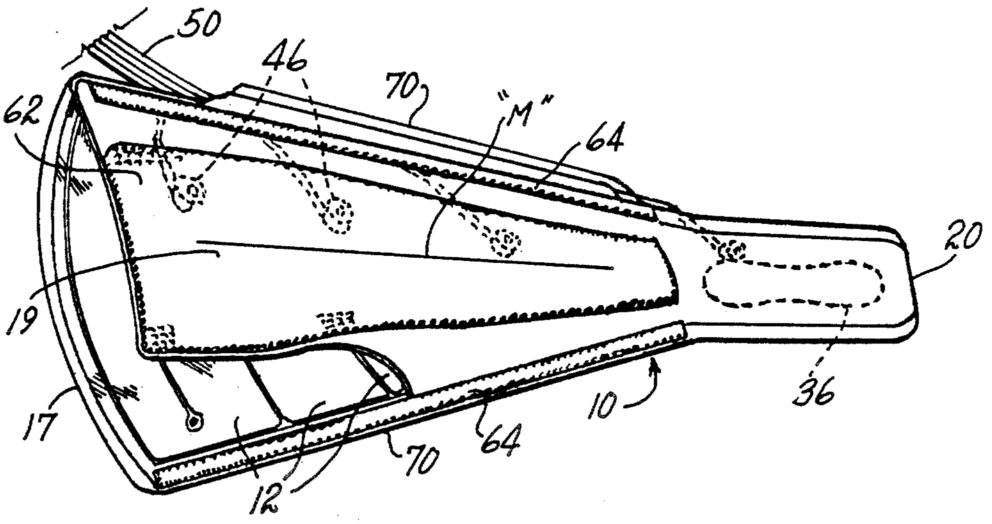
FIG. 1 is a perspective view of a full limb length compressible sleeve constructed according to the principles of the present invention.

A generally rectangular (slightly truncated) patch of receiving cloth 62 is secured to the outside upper portion of the frontside 19, of the sleeve, as shown in FIGS. 1, 2, 3, and 5. A narrow strip 64 of hook means, such as the trademarked "Velcro" material, is attached adjacent the elongated marginal side edges 70, as shown in FIGS. 1, 2, and 5.

After a patient has placed his leg or limb in the sheath-like sleeve 10, the longitudinal side portions along the proximal segment of the sleeve 10, may be wrapped about the patient's limb "L" as shown in FIG. 2, so that the narrow strip 64 of hook means engages the receiving cloth 62 to encircle the patient's limb. A marker line "M" as shown in FIG. 1, may be disposed on the topside of the receiving cloth 62, to facilitate alignment of the sleeve with the front mid-portion of the patient's limb (leg).

Air or other pressurizable fluid may than be directed through the conduits into the chambers 34, 38, 40, 42 and 44 in the sequence and pressure profile created by the pressure generator aforementioned.

In view of the foregoing description and illustrative drawings, it will thus be appreciated that the present invention provides a therapeutic device for applying compressive pressure against the leg, which device is easily applied and removed by the patient and is accordingly particularly suitable for home care.

Apart from this advantage, the construction and arrangement of elements of the therapeutic device of this invention provides further significant advantages which can best be described by reference to the physiology of the patient's leg.

As was previously stated, the important area to be subjected to compression is the muscular area on the sides and particularly on the back of the leg. The front of the leg is bony and hence does not require this treatment. Accordingly, the front side of the sleeve, which comprises the tongue portion thereof, is not provided with sequential compression chambers. Moreover, the tongue portion is inelastic so that compression occurring at the back of the leg causes tension to be applied to the inelastic tongue portion which is in turn translated to pressure over the radius of curvature at the front of the leg.

It will also be seen from the foregoing description that there is no compression applied to the bottom of the foot. Since blood does not pool there, edema does not occur and consequently there is no need to apply compression. On the other hand, if the bottom of the foot portion were inflated to apply compression, the resulting pressure patterns would be changed if the patient stood on his feet, which the patient is indeed permitted to do when wearing the therapeutic device of this invention.

Yet another important advantage is obtained from the use of an outer sheet which is relatively stiff and inelastic and an inner film which is soft and compliant. Apart from the fact that it is desirable to have an abrasion resistant outer surface, this combination of outer sheet and inner film permits the inner film to conform substantially to the shape of the individual leg. Accordingly, zero pressure points are substantially precluded, thus obviating the so-called corrugation effect typically seen when prior hospital compressible sleeve devices are used on edematous legs.

I claim:

1. A method for the manufacture of a limb compressible sleeve to permit a distal to proximal sequential compression of a human limb, comprising the steps of:

fabricating an elongated outer sheet having a first and a second end, with an intermediate portion extending therebetween;

fabricating an elongated inner film having a first and a second end, with an intermediate portion extending therebetween;

juxtaposing said inner film onto said outer sheet to align their peripheries;

bonding generally transverse seal lines across a first longitudinal half only of said juxtaposed sheet and film to define a plurality of compressible chambers therebetween;

bonding generally longitudinal seal lines across the other longitudinal half of said juxtaposed sheet and film to define a compressible chamber therebetween;

folding said second half and said first half together about a lateral fold line; and sealing the common peripheries of said first half and said second half to define a sheath into which a patient may insert a limb.

2. The method of manufacture of a limb compressible sleeve as recited in claim 1, including the step of:

inserting a generally oval pad between the outer sheet and the inner film prior to bonding thereof, to establish a non-compressible cushion in said sleeve for a limb inserted therein.

3. The method of manufacture of a limb compressible sleeve as recited in claim 2, including the steps of:

attaching a gripping surface onto the central front side of folded outer sheet;

attaching gripping strips onto the marginal longitudinal edges of the front side of said outer sheet so that the marginal longitudinal edges may be wrapped over and secured to the gripping surface of the central front side of the folded outer sheet to permit girthwise adjustability of said sleeve around a patient's limb thereindisposed.

4. The method of manufacture of a limb compressible sleeve as recited in claim 3, including the step of;

marking a line along the longitudinal center of the front side of the folded outer sheet to facilitate alignment of the sleeve onto a patient's limb by correspondence of said line with the front portion of a patient's limb.

5. The method of manufacture of a limb compressible sleeve as recited in claim 4, including the step of:

providing a longitudinally directed opening along one side edge of the first half of said sleeve, to facilitate entry of a patient's limb into said sleeve.

* * * * *